United States Patent
Esfandyarpour

(10) Patent No.: US 10,059,982 B2
(45) Date of Patent: *Aug. 28, 2018

(54) NANO-SENSOR ARRAY

(71) Applicant: The Board of Trustees of the Leland Stanford Junior University, Stanford, CA (US)

(72) Inventor: Hesaam Esfandyarpour, Los Altos, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 165 days.

This patent is subject to a terminal disclaimer.

(21) Appl. No.: 15/230,048

(22) Filed: Aug. 5, 2016

(65) Prior Publication Data

US 2016/0340721 A1 Nov. 24, 2016

Related U.S. Application Data

(63) Continuation of application No. 14/081,358, filed on Nov. 15, 2013, now Pat. No. 9,434,983, which is a
(Continued)

(51) Int. Cl.
*C12Q 1/68* (2018.01)
*C12Q 1/6825* (2018.01)
(Continued)

(52) U.S. Cl.
CPC ............ *C12Q 1/6825* (2013.01); *C40B 60/12* (2013.01); *G01N 27/3278* (2013.01);
(Continued)

(58) Field of Classification Search
CPC .. C12Q 1/6825; G01N 33/49; G01N 27/3278; C40B 60/12; Y10T 29/49826; B82Y 15/00; B82Y 40/00
See application file for complete search history.

(56) References Cited

U.S. PATENT DOCUMENTS 2,014,761 A 9/1935 Faust
4,072,576 A 2/1978 Arwin et al.
(Continued)

FOREIGN PATENT DOCUMENTS

CN 1337580 A 2/2002
CN 101120098 A 2/2008
(Continued)

OTHER PUBLICATIONS

Gao et al. Anal. Chem. 2007, 79, 3291-3297. (Year: 2007).*
(Continued)

*Primary Examiner* — Sally A Merkling
(74) *Attorney, Agent, or Firm* — Crawford Maunu PLLC

(57) ABSTRACT

In one embodiment, a method is provided for the manufacture of a nano-sensor array. A base having a sensing region is provided along with a plurality of nano-sensors. Each of the plurality of nano-sensors is formed by: forming a first nanoneedle along a surface of the base, forming a dielectric on the first nanoneedle, and forming a second nanoneedle on the dielectric layer. The first nanoneedle of each sensor has a first end adjacent to the sensing region of the base. The second nanoneedle is separated from the first nanoneedle by the dielectric and has a first end adjacent the first end of the first nanoneedle. The base is provided with a fluidic channel. The plurality of nano-sensors and the fluidic channel are configured and arranged with the first ends proximate the fluidic channel to facilitate sensing of targeted matter in the fluidic channel.

18 Claims, 6 Drawing Sheets

Related U.S. Application Data continuation of application No. 13/118,044, filed on May 27, 2011, now Pat. No. 8,585,973.

(51) Int. Cl.
*C40B 60/12* (2006.01)
*G01N 27/327* (2006.01)
*G01N 33/49* (2006.01)
*B82Y 40/00* (2011.01)
*B82Y 15/00* (2011.01)

(52) U.S. Cl.
CPC .............. *G01N 33/49* (2013.01); *B82Y 15/00* (2013.01); *B82Y 40/00* (2013.01); *Y10T 29/49826* (2015.01)

(56) References Cited

U.S. PATENT DOCUMENTS

| | | |
|---|---|---|
| 5,602,042 A | 2/1997 | Farber |
| 5,612,181 A | 3/1997 | Fourmentin-Guilbert |
| 5,795,782 A | 8/1998 | Church et al. |
| 5,834,197 A | 11/1998 | Parton |
| 6,046,097 A | 4/2000 | Hsieh et al. |
| 6,087,095 A | 7/2000 | Rosenthal et al. |
| 6,210,891 B1 | 4/2001 | Nyren et al. |
| 6,327,410 B1 | 12/2001 | Walt et al. |
| 6,632,655 B1 | 10/2003 | Mehta et al. |
| 6,833,246 B2 | 12/2004 | Balasubramanian |
| 6,953,958 B2 | 10/2005 | Baxter et al. |
| 7,081,192 B1 | 7/2006 | Wang et al. |
| 7,223,540 B2 | 5/2007 | Pourmand et al. |
| 7,242,241 B2 | 7/2007 | Toumazou et al. |
| 7,270,981 B2 | 9/2007 | Armes et al. |
| 7,282,370 B2 | 10/2007 | Bridgham et al. |
| 7,291,496 B2 | 11/2007 | Holm-Kennedy |
| 7,312,085 B2 | 12/2007 | Chou et al. |
| 7,317,216 B2 | 1/2008 | Holm-Kennedy |
| 7,323,305 B2 | 1/2008 | Leamon et al. |
| 7,361,466 B2 | 4/2008 | Korlach et al. |
| 7,399,590 B2 | 7/2008 | Piepenburg et al. |
| 7,435,561 B2 | 10/2008 | Piepenburg et al. |
| 7,485,428 B2 | 2/2009 | Armes et al. |
| 7,615,382 B2 | 11/2009 | Wang et al. |
| 7,645,596 B2 | 1/2010 | Williams et al. |
| 7,649,358 B2 | 1/2010 | Toumazou et al. |
| 7,666,598 B2 | 2/2010 | Piepenburg et al. |
| 7,682,837 B2 | 3/2010 | Jain et al. |
| 7,686,929 B2 | 3/2010 | Toumazou et al. |
| 7,692,219 B1 | 4/2010 | Holm-Kennedy |
| 7,695,907 B2 | 4/2010 | Miyahara et al. |
| 7,763,427 B2 | 7/2010 | Piepenburg et al. |
| 7,824,890 B2 | 11/2010 | Hoser et al. |
| 7,875,440 B2 | 1/2011 | Williams et al. |
| 7,888,013 B2 | 2/2011 | Miyahara et al. |
| 7,932,034 B2 | 4/2011 | Esfandyarpour et al. |
| 7,948,015 B2 | 5/2011 | Rothberg et al. |
| 8,030,000 B2 | 10/2011 | Piepenburg et al. |
| 8,062,848 B2 | 11/2011 | Goldstein et al. |
| 8,062,850 B2 | 11/2011 | Piepenburg et al. |
| 8,071,308 B2 | 12/2011 | Piepenburg et al. |
| 8,114,591 B2 | 2/2012 | Toumazou et al. |
| 8,128,796 B2 | 3/2012 | Ishige et al. |
| 8,129,118 B2 | 3/2012 | Weindel et al. |
| 8,137,569 B2 | 3/2012 | Harnack et al. |
| 8,152,991 B2 | 4/2012 | Briman et al. |
| 8,154,093 B2 | 4/2012 | Bradley et al. |
| 8,173,401 B2 | 5/2012 | Chang et al. |
| 8,179,296 B2 | 5/2012 | Kelly et al. |
| 8,257,925 B2 | 9/2012 | Brown et al. |
| 8,301,394 B2 | 10/2012 | Chen et al. |
| 8,426,134 B2 | 4/2013 | Piepenburg et al. |
| 8,460,875 B2 | 6/2013 | Ames et al. |
| 8,518,670 B2 | 8/2013 | Goldstein et al. |
| 8,574,846 B2 | 11/2013 | Piepenburg et al. |
| 8,580,507 B2 | 11/2013 | Piepenburg et al. |
| 8,585,973 B2 | 11/2013 | Esfandyarpour |
| 8,637,253 B2 | 1/2014 | Piepenburg et al. |
| 8,673,560 B2 | 3/2014 | Leamon et al. |
| 8,969,002 B2 | 3/2015 | Esfandyarpour et al. |
| 9,150,915 B2 | 10/2015 | Esfandyarpour et al. |
| 9,184,099 B2 | 11/2015 | Baghbani-Parizi et al. |
| 9,187,783 B2 | 11/2015 | Esfandyarpour et al. |
| 9,274,077 B2 | 3/2016 | Esfandyarpour et al. |
| 9,399,217 B2 | 7/2016 | Esfandyarpour et al. |
| 9,434,983 B2 | 9/2016 | Esfandyarpour |
| 9,533,305 B2 | 1/2017 | Esfandyarpour et al. |
| 2002/0132245 A1 | 9/2002 | Boles et al. |
| 2002/0148739 A2 | 10/2002 | Liamos et al. |
| 2003/0209432 A1 | 11/2003 | Choong et al. |
| 2004/0014201 A1 | 1/2004 | Kim et al. |
| 2004/0033492 A1 | 2/2004 | Chen |
| 2004/0197793 A1 | 10/2004 | Hassibi et al. |
| 2005/0009022 A1 | 1/2005 | Weiner et al. |
| 2005/0019784 A1 | 1/2005 | Su et al. |
| 2005/0032076 A1 | 2/2005 | Williams et al. |
| 2006/0008824 A1 | 1/2006 | Ronaghi et al. |
| 2006/0105373 A1 | 5/2006 | Pourmand et al. |
| 2006/0222569 A1 | 10/2006 | Barten et al. |
| 2007/0132043 A1 | 6/2007 | Bradley |
| 2007/0184463 A1 | 8/2007 | Molho et al. |
| 2007/0275375 A1 | 11/2007 | Van Eijk |
| 2008/0009420 A1 | 1/2008 | Schroth |
| 2008/0032295 A1 | 2/2008 | Toumazou et al. |
| 2008/0161200 A1 | 7/2008 | Yu et al. |
| 2008/0166727 A1 | 7/2008 | Esfandyarpour et al. |
| 2008/0171325 A1 | 7/2008 | Brown et al. |
| 2008/0176817 A1 | 7/2008 | Zhou et al. |
| 2008/0187915 A1 | 8/2008 | Polonsky et al. |
| 2008/0241841 A1 | 10/2008 | Murakawa et al. |
| 2008/0286762 A1 | 11/2008 | Miyahara et al. |
| 2008/0302732 A1 | 12/2008 | Soh et al. |
| 2008/0318243 A1 | 12/2008 | Haga et al. |
| 2009/0005259 A1 | 1/2009 | Drmanac |
| 2009/0026082 A1 | 1/2009 | Rothberg et al. |
| 2009/0029385 A1 | 1/2009 | Christians et al. |
| 2009/0032401 A1 | 2/2009 | Ronaghi et al. |
| 2009/0048124 A1 | 2/2009 | Leamon et al. |
| 2009/0127589 A1 | 5/2009 | Rothberg et al. |
| 2009/0166221 A1 | 7/2009 | Ishige et al. |
| 2009/0170716 A1 | 7/2009 | Su et al. |
| 2009/0170724 A1 | 7/2009 | Balasubramanian et al. |
| 2009/0181385 A1 | 7/2009 | McKeman et al. |
| 2009/0191594 A1 | 7/2009 | Ohashi |
| 2010/0035252 A1 | 2/2010 | Rothberg et al. |
| 2010/0072080 A1 | 3/2010 | Karhanek et al. |
| 2010/0078325 A1 | 4/2010 | Oliver |
| 2010/0112588 A1 | 5/2010 | Farinas et al. |
| 2010/0137143 A1 | 6/2010 | Rothberg et al. |
| 2010/0137413 A1 | 6/2010 | Cummins et al. |
| 2010/0151479 A1 | 6/2010 | Toumazou et al. |
| 2010/0159461 A1 | 6/2010 | Toumazou et al. |
| 2010/0163414 A1 | 7/2010 | Gillies et al. |
| 2010/0167938 A1 | 7/2010 | Su et al. |
| 2010/0188073 A1 | 7/2010 | Rothberg et al. |
| 2010/0197507 A1 | 8/2010 | Rothberg et al. |
| 2010/0209922 A1 | 8/2010 | Williams et al. |
| 2010/0255595 A1 | 10/2010 | Toumazou et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0317531 A1 | 12/2010 | Balasubramanian et al. |
| 2010/0330570 A1 | 12/2010 | Vander Horn et al. |
| 2011/0039266 A1 | 2/2011 | Williams et al. |
| 2011/0117026 A1 | 5/2011 | Tseng et al. |
| 2011/0118139 A1 | 5/2011 | Mehta et al. |
| 2011/0123991 A1 | 5/2011 | Hoser |
| 2011/0159481 A1 | 6/2011 | Liu et al. |
| 2011/0171655 A1 | 7/2011 | Esfandyarpour et al. |
| 2011/0177498 A1 | 7/2011 | Clarke et al. |
| 2011/0183321 A1 | 7/2011 | Williams et al. |
| 2011/0195253 A1 | 8/2011 | Hinz et al. |

(56) References Cited

U.S. PATENT DOCUMENTS

| | | |
|---|---|---|
| 2011/0195459 A1 | 8/2011 | Hinz et al. |
| 2011/0201506 A1 | 8/2011 | Hinz et al. |
| 2011/0217697 A1 | 9/2011 | Rothberg et al. |
| 2011/0230375 A1 | 9/2011 | Rothberg et al. |
| 2011/0241081 A1 | 10/2011 | Rothberg et al. |
| 2011/0247933 A1 | 10/2011 | Rothberg et al. |
| 2011/0248319 A1 | 10/2011 | Rothberg et al. |
| 2011/0248320 A1 | 10/2011 | Rothberg et al. |
| 2011/0259745 A1 | 10/2011 | Dehlinger et al. |
| 2011/0263463 A1 | 10/2011 | Rothberg et al. |
| 2011/0287432 A1 | 11/2011 | Wong et al. |
| 2011/0287945 A1 | 11/2011 | Rothberg et al. |
| 2011/0294115 A1 | 12/2011 | Williams et al. |
| 2011/0311979 A1 | 12/2011 | Brown et al. |
| 2012/0013392 A1 | 1/2012 | Rothberg et al. |
| 2012/0021918 A1 | 1/2012 | Bashir et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0061255 A1 | 3/2012 | Rothberg et al. |
| 2012/0061256 A1 | 3/2012 | Rothberg et al. |
| 2012/0061733 A1 | 3/2012 | Rothberg et al. |
| 2012/0065093 A1 | 3/2012 | Rothberg et al. |
| 2012/0071363 A1 | 3/2012 | Rothberg et al. |
| 2012/0085660 A1 | 4/2012 | Rothberg et al. |
| 2012/0088682 A1 | 4/2012 | Rothberg et al. |
| 2012/0094871 A1 | 4/2012 | Hinz et al. |
| 2012/0129173 A1 | 5/2012 | Pienburg et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0135893 A1 | 5/2012 | Drmanac et al. |
| 2012/0138460 A1 | 6/2012 | Baghbani-Parizi et al. |
| 2012/0156728 A1 | 6/2012 | Li et al. |
| 2012/0157322 A1 | 6/2012 | Myllykangas et al. |
| 2012/0173159 A1 | 7/2012 | Davey et al. |
| 2012/0175252 A1 | 7/2012 | Toumazou et al. |
| 2012/0222496 A1 | 9/2012 | Mamigonias |
| 2012/0258456 A1 | 10/2012 | Armes et al. |
| 2012/0258499 A1 | 10/2012 | Piepenburg et al. |
| 2012/0264617 A1 | 10/2012 | Petit |
| 2012/0295819 A1 | 11/2012 | Leamon et al. |
| 2012/0302454 A1 | 11/2012 | Esfandyarpour |
| 2012/0322113 A1 | 12/2012 | Erlander et al. |
| 2013/0005613 A1 | 1/2013 | Leamon et al. |
| 2013/0023011 A1 | 1/2013 | Leamon et al. |
| 2013/0059290 A1 | 3/2013 | Armes |
| 2013/0059762 A1 | 3/2013 | Leamon et al. |
| 2013/0090860 A1 | 4/2013 | Sikora et al. |
| 2013/0096013 A1 | 4/2013 | Esfandyarpour et al. |
| 2013/0109577 A1 | 5/2013 | Korlach et al. |
| 2013/0203634 A1 | 8/2013 | Jovanovich et al. |
| 2013/0225421 A1 | 8/2013 | Li et al. |
| 2013/0231254 A1 | 9/2013 | Kawashima et al. |
| 2013/0281307 A1 | 10/2013 | Li et al. |
| 2014/0045701 A1 | 2/2014 | Esfandyarpour et al. |
| 2014/0057339 A1 | 2/2014 | Esfandyarpour et al. |
| 2014/0099674 A1 | 4/2014 | Piepenburg et al. |
| 2014/0235457 A1 | 8/2014 | Esfandyarpour et al. |
| 2014/0329699 A1 | 11/2014 | Esfandyarpour |
| 2015/0148264 A1 | 5/2015 | Esfandyarpour et al. |
| 2015/0344943 A1 | 12/2015 | Oberstrass |
| 2015/0376692 A1 | 12/2015 | Esfandyarpour et al. |
| 2016/0076097 A1 | 3/2016 | Esfandyarpour et al. |
| 2016/0077049 A1 | 3/2016 | Baghbani-Parizi et al. |
| 2016/0273032 A1 | 9/2016 | Esfandyarpour et al. |
| 2017/0065977 A1 | 3/2017 | Esfandyarpour et al. |
| 2017/0073750 A1 | 3/2017 | Esfandyarpour et al. |

FOREIGN PATENT DOCUMENTS

| | | |
|---|---|---|
| CN | 101848757 A | 9/2010 |
| EP | 0676623 A2 | 10/1995 |
| EP | 1499738 B1 | 7/2008 |
| EP | 1992706 A2 | 11/2008 |
| EP | 2290096 A2 | 3/2011 |
| JP | 2006512583 A | 4/2006 |
| JP | 2008525822 A | 7/2008 |
| JP | 2010513869 A | 4/2010 |
| JP | 2010517040 A | 5/2010 |
| JP | 2010517041 A | 5/2010 |
| JP | 2010518401 A | 5/2010 |
| WO | WO0118246 A1 | 3/2001 |
| WO | WO0137958 A2 | 5/2001 |
| WO | WO0142508 A2 | 6/2001 |
| WO | WO0227909 A2 | 4/2002 |
| WO | WO02061146 A1 | 8/2002 |
| WO | WO2004027024 A2 | 4/2004 |
| WO | WO2005008450 A2 | 1/2005 |
| WO | WO2005108612 A2 | 11/2005 |
| WO | WO2005121363 A2 | 12/2005 |
| WO | WO2006050346 A2 | 5/2006 |
| WO | WO2007041619 A2 | 4/2007 |
| WO | WO2007098049 A2 | 8/2007 |
| WO | WO2008076406 A2 | 6/2008 |
| WO | WO2009012112 A1 | 1/2009 |
| WO | WO2009052348 A2 | 4/2009 |
| WO | WO2009074926 A1 | 6/2009 |
| WO | WO2009122159 A2 | 10/2009 |
| WO | WO2009150467 A1 | 12/2009 |
| WO | WO2010008480 A2 | 1/2010 |
| WO | WO2010026488 A2 | 3/2010 |
| WO | WO2010037085 A1 | 4/2010 |
| WO | WO2010041231 A2 | 4/2010 |
| WO | WO2010047804 A1 | 4/2010 |
| WO | WO2010075188 A2 | 7/2010 |
| WO | WO2010138187 A1 | 12/2010 |
| WO | WO2010141940 A1 | 12/2010 |

OTHER PUBLICATIONS

Gao, et al. Silicon nanowire arrays for label-free detection of DNA. Anal Chem. May 1, 2007;79(9):3291-7. Epub Apr. 4, 2007.
Office Action dated Mar. 4, 2016 for U.S. Appl. No. 14/081,358.
Office Action dated Oct. 5, 2015 for U.S. Appl. No. 14/081,358.
Brouns, et al.,Small CRISPR RNAs guide antiviral defense in prokaryotes.,Science,Aug. 15, 2008,321(5891),960-4.
Cagnin, et al. Overview of electrochemical DNA biosensors: new approaches to detect the expression of life. Sensors (Basel). 2009;9(4):3122-48. doi: 10.3390/s90403122. Epub Apr. 24, 2009.
Carte, et al.,Cas6 is an endoribonuclease that generates guide RNAs for invader defense in prokaryotes.,Genes Dev., Dec. 15, 2008,22(24),3489-96.
Cho, et al.,Bis-aptazyme sensors for hepatitis C virus replicase and helicase without blank signal.,Nucleic Acids Res,Nov. 27, 2005,33(20),e177.
Daniels, et al. Label-Free Impedance Biosensors: Opportunities and Challenges. Electroanalysis. May 16, 2007;19 (12):1239-1257.
Daniels, et al. Simultaneous Measurement of Nonlinearity and Electrochemical Impedance for Protein Sensing Using Two-Tone Excitation. 30th Annual International IEEE EMBS Conference. Vancouver, British Columbia, Canada, Aug. 20-24, 2008. 5753-5756.
Dimov, et al.,Stand-alone self-powered integrated microfluidic blood analysis system (SIMBAS).,Lab Chip,Mar. 7, 2011,11(5),845-50.
Edman, et al.,Electric field directed nucleic acid hybridization on microchips.,Nucleic Acids Res.,Dec. 15, 1997,25 (24),4907-14.
Ellington, et al.,In vitro selection of RNA molecules that bind specific ligands.,Nature, Aug. 30, 1990,346 (6287),818-22.
Esfandyarpour, et al. A Novel Nanoneedle Biosensor for DNA Sequencing (abstract). Dec. 31, 2008. Available at http://www.nsti.org/Nanotech2008/showabstract.html?absno=1522.

(56) References Cited

OTHER PUBLICATIONS

Finn, et al. Efficient incorporation of positively charged 2', 3'-dideoxynucleoside-5'-triphosphates by DNA polymerases and their application in 'direct-load' DNA sequencing. Nucleic Acids Res. Aug. 15, 2003;31(16):4769-78.
Gardeniers, et al.,Silicon micromachined hollow microneedles for transdermal liquid transport., Microelectromechanical Systems,2003,12(6),855-862.
Haurwitz, et al.,Sequence- and structure-specific RNA processing by a CRISPR endonuclease.,Science, Sep. 10, 2010,329(5997),1355-8.
Hollis, et al. Structure of the gene 2.5 protein, a single-stranded DNA binding protein encoded by bacteriophage T7. Proc Natl Acad Sci U S A. Aug. 14, 2001;98(17):9557-62. Epub Jul. 31, 2001.
Javanmard, et al. A microfluidic platform for electrical detection of DNA hybridization. Sens Actuators B Chem. May 20, 2011;154(1):22-27. Epub Mar. 30, 2010.
Kaushik, et al.,Lack of pain associated with microfabricated microneedles.,Anesth Analg, Feb. 2001,92(2),502-4.
Kim, et al.,Replication of DNA microarrays prepared by in situ oligonucleotide polymerization and mechanical transfer., Anal Chem,Oct. 1, 2007,79(19),7267-74.
Kitano, et al. Molecular structure of RNA polymerase and its complex with DNA. J Biochem. Jan. 1969;65(1):1-16.
Kunin, et al.,Evolutionary conservation of sequence and secondary structures in CRISPR repeats.,Genome Biol, 2007,8(4),R61.
Kurosaki, et al.,Rapid and simple detection of Ebola virus by reverse transcription-loop-mediated isothermal amplification., J Virol Methods, Apr. 2007,141(1),78-83.
Lee, et al. Ion-sensitive field-effect transistor for biological sensing. Sensors (Basel). 2009;9(9):7111-31. doi: 10.3390/s90907111. Epub Sep. 7, 2009.
Lin, et al.,Replication of DNA microarrays from zip code masters.,J Am Chem Soc, Mar. 15, 2006,128(10),3268-72.
Liu, et al.,Immobilization of DNA onto poly(dimethylsiloxane) surfaces and application to a microelectrochemical enzyme-amplified DNA hybridization assay.,Langmuir.,Jul. 6, 2004,20(14),5905-10.
Makarova, et al.,A putative RNA-interference-based immune system in prokaryotes: computational analysis of the predicted enzymatic machinery, functional analogies with eukaryotic RNAi, and hypothetical mechanisms of action., Biol Direct, Mar. 16, 2006,1:7,26 pages.
Manickam, et al. A CMOS Electrochemical Impedance Spectroscopy (EIS) Biosensor Array. IEEE Trans Biomed Circuits Syst. Dec. 2010;4(6):379-90. doi: 10.1109/TBCAS.2010.2081669.
Margulies, et al. Genome sequencing in microfabricated high-density picolitre reactors. Nature. Sep. 15, 2005;437 (7057):376-80. Epub Jul. 31, 2005.
Notomi, et al.,Loop-mediated isothermal amplification of DNA.,Nucleic Acids Res,Jun. 15, 2000,28(12),E63.
Piepenburg, et al. DNA detection using recombination proteins. PLoS Biol. Jul. 2006;4(7):e204.
Ren, et al. Rapid and sensitive detection of hepatitis B virus 1762T/1764A double mutation from hepatocellular carcinomas using LNA-mediated PCR clamping and hybridization probes. Journal of Virological Methods. 2009; 158:24-29.
Sabounchi, et al. Sample concentration and impedance detection on a microfluidic polymer chip. Biomed Microdevices. Oct. 2008;10(5):661-70. doi: 10.1007/s10544-008-9177-4.
Senapati, et al. A nonamembrane-based nucleic acid sensing platform for portable diagnostics. Topics in Current Chemistry. 2011; 304:153-169.
Sivamani, et al.,Microneedles and transdermal applications.,Expert Opin Drug Deliv,Jan. 2007,4(1),19-25.
Sosnowski, et al.,Rapid determination of single base mismatch mutations in DNA hybrids by direct electric field control.,Proc Natl Acad Sci U S A.,Feb. 18, 1997,94(4),1119-23.
Van Der Oost, et al.,CRISPR-based adaptive and heritable immunity in prokaryotes.,Trends Biochem Sci., Aug. 2009,34(8),401-7.
Voelkerding, et al. Next generation sequencing: from basic research to diagnostics. Clin. Chem. 2009; 55 (4):641-658.
Wang, et al.,Interaction of the Cas6 riboendonuclease with CRISPR RNAs: recognition and cleavage.,Structure,Feb. 9, 2011,19(2),257-64.
Zhang, et al.,Dielectrophoresis for manipulation of micro/nano particles in microfluidic systems.,Anal Bioanal Chem.,Jan. 2010,396(1),401-20.
C. Guiducci, C. Stagni, G. Zuccheri, A. Bogliolo, L. Benini, B. Samori, and B. Ricco, "A Biosensor for Direct Detection of DNA Sequences Based on Capacitance Measurements," ESSDERC 2002, pp. 479-482 (2002).
C. Bell, J. Uhl, T. Hadfield, J. David, R. Meyer, T. Smith, and F. Cockerill III, "Detection of Bacillus anthracis DNA by LightCycler PCT," J. Clin Microbiol. 40:2897-2902 (Aug. 2002).
J.E. Andreotti, et al. "Immunoassay of infectious agents," BioTechniques Euro Edition 35, pp. 850-859 (Oct. 2003).
F. Patolsky, G. Zheng, O. Hayden, M. Lakadamyali, X. Zhuang, and C. Leiber, "Electrical detection of single viruses," Proc Natl Acad Sci USA, vol. 101, No. 39 pp. 14017-14022 (Sep. 2004).
M. Yazdanpanah, S. Harfenist, A. Safir, and R. Cohn, "Selective self-assembly at room temperature of individual freestanding Ag2Ga alloy nanoneedles," J. Appl. Phys. 98, pp. 073510-073517 (2005).
G. Zheng, et al., "Multiplexed electrical detection of cancer markers with nanowire sensor arrays," Nature Biotechnology 23, pp. 1294-1301 (2005).
H. Boo, R.-A. Jeong, S. Park, K.-S. Kim, K.-H. An, Y.-H. Lee, J.-H. Han, H.-C. Kim, and T.-D. Chung, "Electrochemical Nanoneedle Biosensor Based on Multiwall Carbon Nanotube," Analytical Chemistry, vol. 78, No. 2, pp. 617-620 (2006).
A. Safir, M. Yazdanpanah, S. Pabba, S.Cambron, F. Zamborini, R. Keynton, and R. Cohn, "Fabrication of an Insulated Probe on a Self-Assembled Metallic Nanowire for Electrochemical Probing in Cells," IEEE (2006).
F. Patolsky, G. Zheng, and C. Lieber, "Fabrication of Silicon Nanowire Devices for Ultrasensitive, Label-free, Real-Time Detection of Biological and Chemical Species," Nature Protocol, vol. 1, No. 4, pp. 1711-1724 (Nov. 2006).
H. Esfandyarpour , A. Maiyegun , and R.W. Davis "3D Modeling of Impedance Spectroscopy for Protein Detection in Nanoneedle Biosensors," Proceedings of the International COMSOL Conference 2007, Boston, MA, USA, pp. 169-173 (Oct. 4-6, 2007).
M. Javanmard, H.Esfandyarpour, F. Pease, and R.W. Davis, "Electrical Detection of Proteins and DNA Using Bioactivated Microfluidic Channels: Theoretical and Experimental Considerations," J. Vac. Sci. Technol. B. 27(6), pp. 3099-3103 (Nov./Dec. 2009).
F. Roosen-Runge, M. Hennig, T. Seydel, F. Zhang, M. W.A. Skoda, S. Zorn, R. Jacobs, M. Maccarini, P. Fouquet and F. Schreiber, "Protein Diffusion in Crowded Electrolyte Solutions," Biochimica et Biophysica Acta 1804, pp. 68-75 (2010).
H. Esfandyarpour, B. Zheng, R.F.W. Pease, ad R.W. Davis,"Geometrical Optimization of Pyrophosphate Concentration in Thermosequencing Platform for DNA Sequencing," Int'l COMSOL Conf., Proc., pp. 169-173 (Oct. 4-6, 2007).

\* cited by examiner

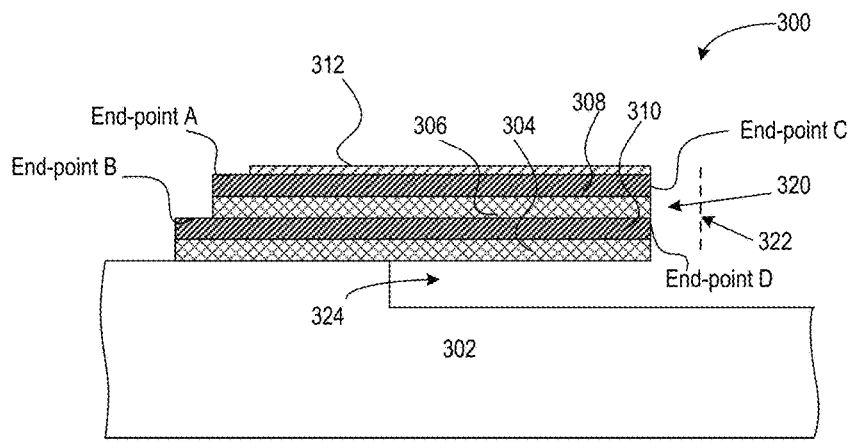
FIG. 3
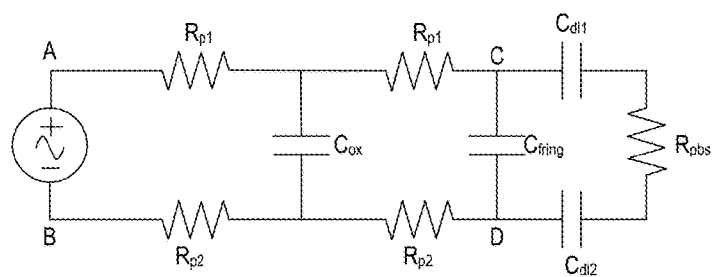
FIG. 4a
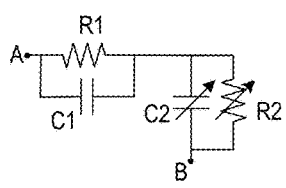       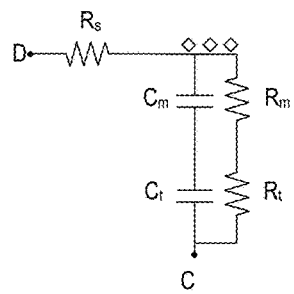       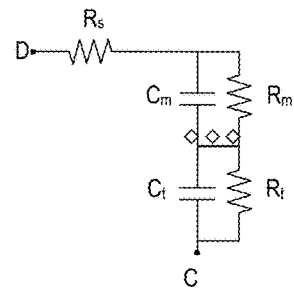
FIG. 4b       FIG. 4c       FIG. 4d

NANO-SENSOR ARRAY

STATEMENT OF GOVERNMENTAL SUPPORT

This invention was made with Government support under contract HG000205 awarded by the National Institutes of Health. The U.S. Government has certain rights in this invention.

FIELD OF THE INVENTION

The present invention relates to chemical and biological particle detection.

BACKGROUND OF THE INVENTION

Biosensors are used for detecting the presence of a target chemical or biological agent in a wide variety of applications, such as detection of contaminants in air (e.g., in air quality sensors) or detecting the presence of proteins and nucleic acids in blood samples or other samples. A biosensor measures the presence of various chemical components in a sample contained within a biosensor cell. For example, a biosensor may be used to measure the amount of glucose present in a sample of blood.

Some known methods of detection rely on growth cultures. These methods are based on the ability of pathogenic species to multiply in nutrient-rich medium containing selective agents that inhibit the growth of non-target organisms. These detection methods may be used to differentiate between target and non-target organisms. Although sensitive and accurate, these procedures can take as long as several days and thus are not useful for organisms that don't grow easily. Other methods of detection, such as Polymerase Chain Reaction (PCR) and Enzyme-linked Immunosorbant Assay (ELISA), can directly detect pathogen-specific DNA and proteins, respectively, and can be completed in a matter of hours. PCR is extremely sensitive and has been shown to detect as few as 10 or fewer organisms. In comparison, ELISA is less sensitive but has the ability to detect proteinaceous toxins. Together, these techniques can provide highly sensitive and specific detection of pathogens and they are currently the standard techniques used in both the clinics and research laboratories.

Detection of events such as binding of single cells or molecules is generally performed using either optical (usually fluorescent) or electrical detection. Optical techniques are very sensitive and can detect single molecule events but require the attachment of a fluorophore molecule to the target. Optical techniques are more sensitive than are thermal or electrical detection because in optical detection, excitement from a single or few photons, in a process such as electron multiplying or Avalanche phenomena, can be amplified and is sufficient to generate a detectable flow of electrons or charge (current). The ability of a microscope to view simultaneously a large area may be the key. While the fluorescent platforms usually have higher sensitivity and signal to noise ratio (SNR) compared to electrical biosensors, they may not provide real time monitoring possible with electrical biosensors.

Electrical detection method techniques may not require the attachment of fluorophores or other labels but are less sensitive. The devices usually suffer from low signal to noise ratio (SNR) due to different sources of noise (e.g. electrical, thermal, Flicker, Johnson, etc.) and low detection signal (e.g. the signal generated due to a reaction or binding event of a target molecule to the probe molecule is not large enough). As a result, electrical biosensors exhibit lower sensitivity, in comparison to the some optical detection techniques, which can be detrimental to early stage detection and diagnosis.

One or more embodiments may address one or more of the above issues.

SUMMARY

Various aspects of one or more embodiments are directed to nano-sensors and the fabrication thereof.

In one embodiment, a method is provided for the manufacture of a nano-sensor array. A base is provided along with a plurality of nano-sensors. Each of the plurality of nano-sensors is formed by forming a first nanoneedle along a surface of the base, forming a dielectric on the first nanoneedle, and forming a second nanoneedle on the dielectric layer. The first nanoneedle of each sensor has a first end adjacent to a region of the base. The second nanoneedle is separated from the first nanoneedle by the dielectric and has a first end adjacent the first end of the first nanoneedle. The plurality of nano-sensors and the fluidic channel are configured and arranged with the first ends in the region to facilitate sensing of targeted matter in the region.

In another embodiment, a nano-sensor array is provided. The nano-sensor array includes a base layer and a plurality of nano-sensors. Each nano-sensor includes a first nanoneedle along a surface of the base, a dielectric layer on the first nanoneedle, and a second nanoneedle on the dielectric layer. The first nanoneedle has a first end in a region. The second nanoneedle is separated from the first nanoneedle by the dielectric and has a first end adjacent to the first end of the first nanoneedle. A probe may be provided on an exposed portion of the dielectric between the first and second nanoneedles at the first end of the second nanoneedle. The probe is configured and arranged to bind to particles of a target type that are present in the fluidic channel. A detection circuit is coupled to a second end of each of said nanoneedles. The detection circuit is configured and arranged to detect a change of impedance between the first and second nanoneedles of each nano-sensor that may result from the binding of a particle of the target type to the respective probe.

In yet another embodiment, a method of detecting the presence of target particles in a sample is provided. The sample is received in a fluidic channel of a base. One or more target particles in the sample are bound to a probe attached to one or more nano-sensors. Each of the one or more nano-sensors includes a first nanoneedle along a surface of the base, a dielectric layer on the first nanoneedle, and a second nanoneedle on the dielectric layer. The first nanoneedle has a first end within the fluidic channel. The second nanoneedle is separated from the first nanoneedle by the dielectric and has a first end adjacent to the first end of the first nanoneedle. The probe is located on an exposed portion of the dielectric between the first and second nanoneedles at the first end of the second nanoneedle. A change of impedance between the first and second nanoneedles of the one or more nano-sensors is detected. The change impedance results from the binding of one of the one or more target particles to the probe of the nano-sensor.

It will be appreciated that various other embodiments are set forth in the Detailed Description and Claims, which follow.

BRIEF DESCRIPTION OF THE DRAWINGS

Various aspects and advantages of the disclosed embodiments will become apparent upon review of the following detailed description and upon reference to the drawings in which:

FIG. 2b shows cross section 1 of the nano-sensor array shown in FIG. 2a;

FIG. 2c shows cross section 2 of the nano-sensor array shown in FIG. 2a;

FIG. 2d shows cross section 3 of the nano-sensor array shown in FIG. 2a;

FIG. 3 shows a cross section of one implementation of a horizontal nanoneedle-sensor that may be used to implement a nano-sensor array;

FIG. 4a shows a circuit diagram of an electrical model of the horizontal nanoneedle-sensor shown in FIG. 3;

FIG. 4b shows a circuit diagram of an electrical model of the impedance between endpoints A and B of the horizontal nanoneedle-sensor shown in FIG. 3;

FIG. 4c shows a circuit diagram illustrating the electrical behavior of the horizontal nanoneedle-sensor shown in FIG. 3 resulting from in a first particle binding scenario;

FIG. 4d shows a circuit diagram illustrating the electrical behavior of the horizontal nanoneedle-sensor shown in FIG. 3 resulting from a second particle binding scenario;

FIG. 5b shows cross section 1 of the nano-sensor array shown in FIG. 5a;

FIG. 5c shows cross section 2 of the nano-sensor array shown in FIG. 5a;

FIG. 5d shows cross section 3 of the nano-sensor array shown in FIG. 5a;

DETAILED DESCRIPTION

In one or more embodiments, a cost effective nano-sensor array is provided having a plurality of horizontal nano-sensors having sensing ends formed above a channel region of a base. The sensing ends of the nano-sensors are configured to bind with target particles present in a sample present in the channel. The unique structure of the horizontal nano-sensors exhibits a change in impedance between two terminals of the nano-sensor in response to the binding of target particles. Using this structure, the presence of target particles of interest may be electrically detected with high sensitivity by measuring the impedance of the sensors. In this manner, target particles may be electrically detected with high sensitivity without the use of fluorophores or other labels. The examples and embodiments discussed herein may be described with reference to the detection of either particles or molecules and such terms are used interchangeably herein.

The horizontal nano-sensors may be fabricated using a simplified manufacturing flow having reduced complexity and increased throughput in comparison to known nanoneedle fabrication methodologies. Due to the simplified flow, a cost effective on-die nano-sensor array may be implemented with a large number of nano-sensors (on the order of thousands, tens of thousands, or millions).

In one or more embodiments, the nano-sensor array may implement impedance detection circuitry on-chip alongside a large number of nano-sensors, which are distributed along various locations within or adjacent to a fluidic channel. By increasing the number of nano-sensors, a large sample area may be tested simultaneously, resulting in reduced testing time, increased sensitivity, and ability to perform a larger number of different tests with reduced reagent usage.

In some embodiments, different tests may be performed by different nanoneedles, by binding different probes to different nanoneedles. Instead of attaching probes simultaneously to all nanoneedle active areas, which may include the nanoneedles and/or the dielectric between the nanoneedles, a photoactivatable moiety may be bound to the active areas of said nanoneedles. Subsequently, in a step which may be repeated as many times as needed, to bind as many different probes as may be desired, different photoactivatable moieties may be activated by, for example, a laser, prior to or concurrently with the introduction of a probe, which may have a linker moiety which may bind to said activated moiety.

Figure 1:
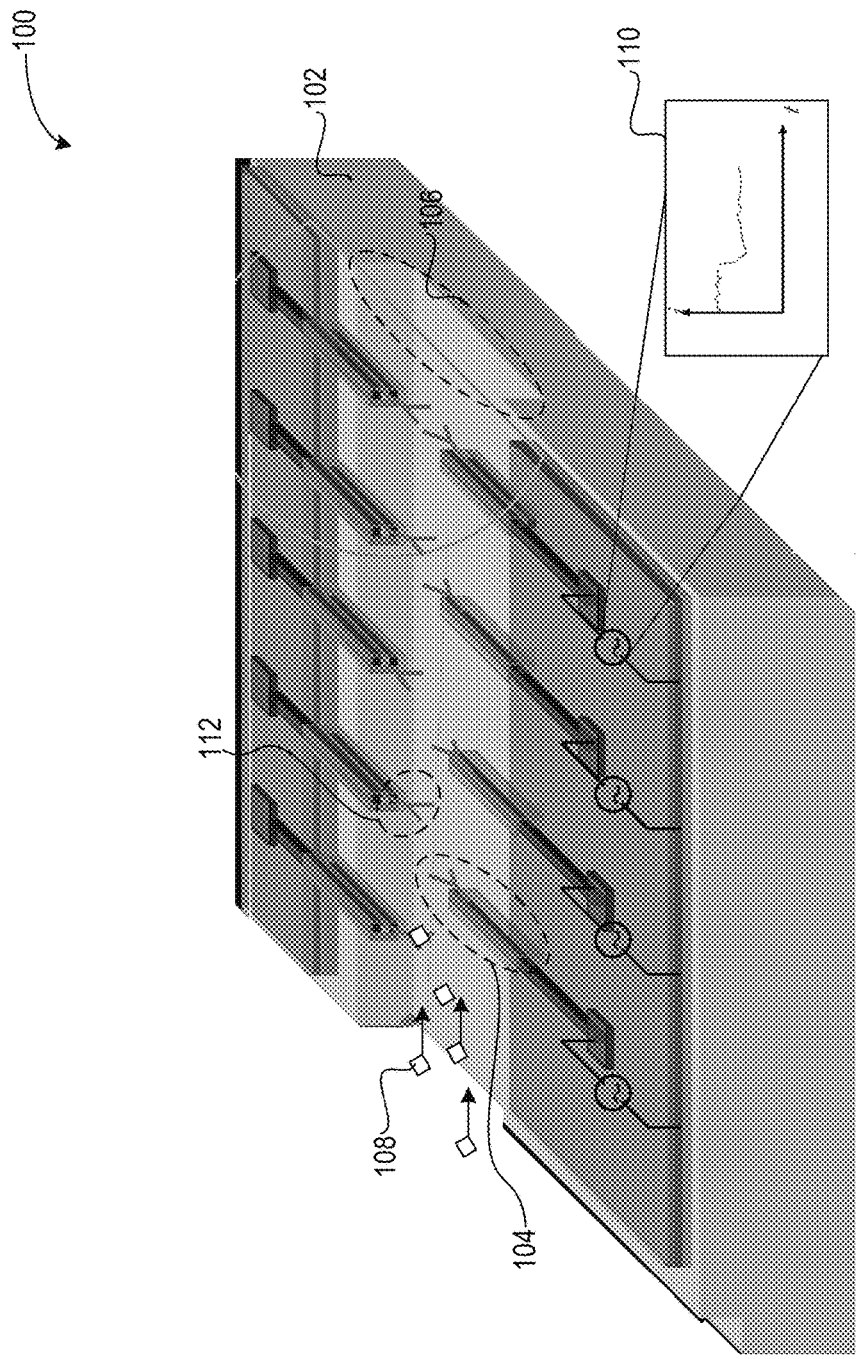
FIG. 1 shows a 3-dimensional view of a nano-sensor array having a plurality of horizontal nano-sensors.

FIG. 1 shows a 3-dimensional view of a nano-sensor array having a plurality of horizontal nano-sensors. The nano-sensor array 100 includes base 102 with a channel 106. The base may consist solely of a substrate layer or may comprise a substrate having one or more layers of material formed on the substrate. A plurality of nano-sensors 104 are formed horizontally on the base 102 overhanging the channel 106. The nano-sensors 104 are each configured to include a probe or probes 112 on a first end of the nano-sensors 104 located overhanging the channel 106. The probe or probes is/are designed to bind with a particular type of particle to be detected. Different nano-sensors may be configured with different probes to allow different types of particles to be detected in the same sample. Different probes may have different shapes. For ease of illustration and description, probes may be depicted herein as Y forked segments, which are not intended to provide an accurate representation of an actual probe.

During operation, a sample to be tested is passed through the channel. The sample may be presented at an edge of the channel 106 and drawn into the channel via pressure and/or capillary forces or may be otherwise delivered into the channel by other means. As particles in the sample 108 pass through the channel and interact with the sensor, particles that are the target type to be detected bind with the probes 112. The horizontal nano-sensors exhibit a change in impedance as a result of a target particle 108 binding with the probe 112 attached to the end of the nano-sensor 104.

The impedance may be measured across two terminals of the nano-sensor 104 as depicted by impedance graph 110 using known impedance detection techniques. For example, impedance can be determined by measuring the small signal AC currents and voltages. For the input, the voltage is measured across the input terminals and the current measured by inserting the meter in series with the signal generator. One may use a fixed frequency, for example 1 kHz, and set the generator level to, for example, around 20 mV RMS. For example, in the case where one applies 20 mV RMS and measures 10 uA for current, then the impedance is 2 k. With high impedance circuits, the current will become very small and difficult to measure, so an alternative method is called for, such as using a fixed resistor and measuring AC voltage at points across the resistor utilizing for example, a trans-impedance amplifier, according to known principles of circuit analysis, or using other known methods to amplify the current prior to measurement of said current.

For clarity and ease of illustration, the embodiments described herein are primarily illustrated and described with reference to an uncovered channel formed in a base. It is recognized the embodiments are primarily envisioned as having a covered channel but may alternatively have an uncovered channel in some embodiments. The cover may also include a fluidic channel formed on the bottom of the cover and aligned with the fluidic channel of the base. It is recognized that the cover applied over the channel may be composed of any of a variety of materials including PDMS, Glass, Plastic, Silicon, etc.

Figure 2A:
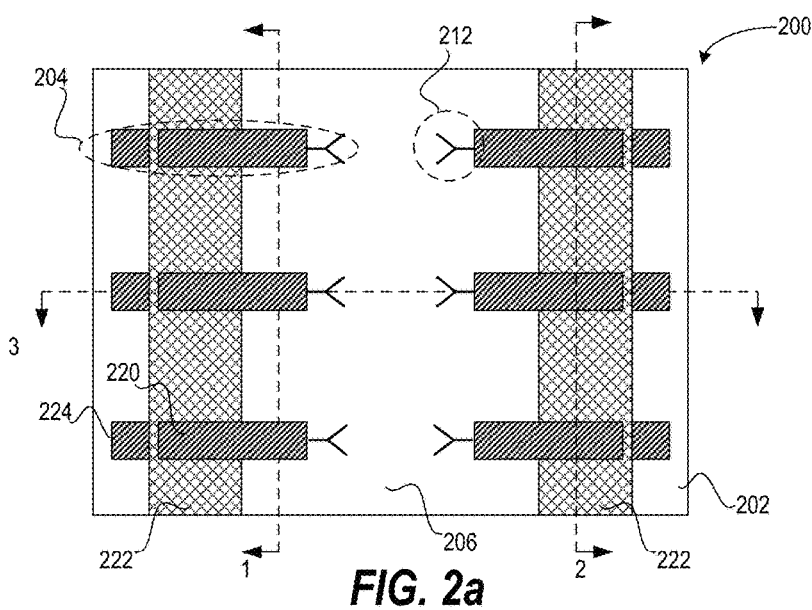
FIG. 2a shows a top view of a second nano-sensor array having a plurality of horizontal nano-sensors.
Figure 2B:
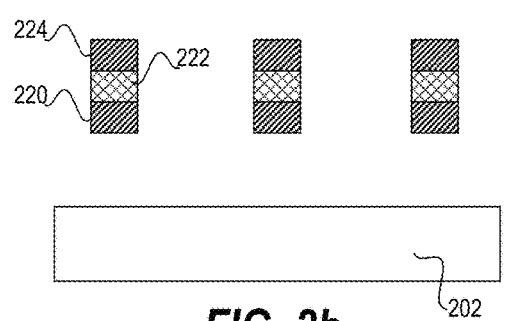
Figure 2C:
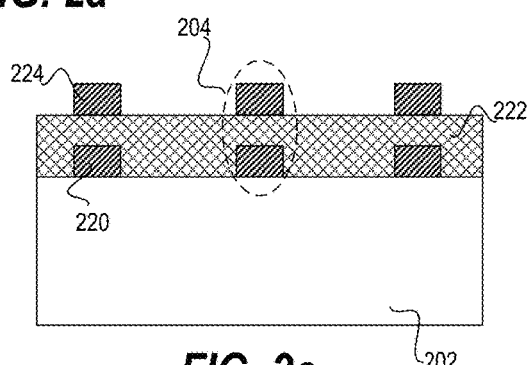
Figure 2D:
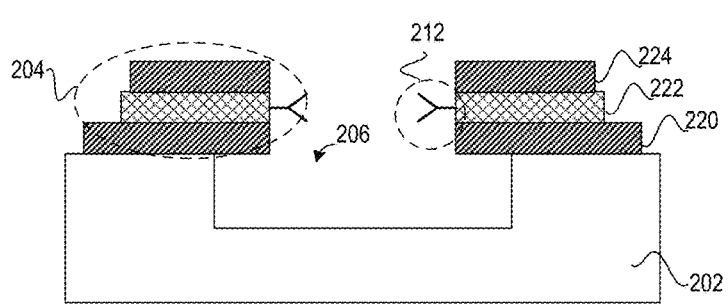

FIGS. 2a-2d show top and cross sectional views of a nano-sensor array similar to that shown in FIG. 1. FIG. 2a shows a top view of a second nano-sensor array having a plurality of horizontal nano-sensors; FIG. 2b shows cross section 1 of the nano-sensor array shown in FIG. 2a; FIG. 2c shows cross section 2 of the nano-sensor array shown in FIG. 2a; and FIG. 2d shows cross section 3 of the nano-sensor array shown in FIG. 2a. The nano-sensor array 200 includes a base 202 with a channel 206 formed in the base. A plurality of nano-sensors 204 are formed horizontally the base 202 and overhang a portion of the channel 206.

As described with reference to the nano-sensor shown in FIG. 1, the nano-sensors 204 are each configured to include a probe 212 on a first end of the nano-sensors 204, which overhangs the channel 206 (probe 212 not shown in cross sections). During operation, a sample to be tested passes through the channel and particles that are the target type (not shown) bind with the probes upon contact.

The horizontal nano-sensors 204 are implemented with a first nanoneedle 220, a dielectric 222, and second nanoneedle 224 arranged in a vertical stack with the dielectric 222 separating the first and second nanoneedles. The lower nanoneedle 220 is formed along a surface of the base 202. In this illustrated implementation, the dielectric 222 is also formed between adjacent ones of the nano-sensors 204, and provides a vertical extension to the sidewalls of the channel 206. It is understood that additional layer(s) may also be formed over the nano-sensors or between the nano-sensors and the base. In this example, probes 212 are affixed to dielectric 222 at the end of the nano-sensor overhanging the channel 206. Alternatively, the probe may be affixed to the first and/or second nanoneedles 220 and 224, or may be provided on the first and/or second nanoneedle and on the dielectric between the first and second nanoneedle.

In some embodiments, an optional passivation or oxidation layer(s) (not shown) may be formed to cover various portioned of the nanoneedles to reduce the surface area of the nanoneedle which may be available for binding or interaction with the fluid.

The horizontal nano-sensors 204 each exhibit an impedance between nanoneedles 220 and 224 that is related to a number of target particles bound with the probe 212 attached to the end of the nano-sensor 204. In this illustrated implementation, a second end of each of the nanoneedles 220 and 224 is left exposed and may be used as terminals to measure impedance between the nanoneedles of the nano-sensor. In some implementations, contact or bonding pads (not shown) may also be formed on the exposed portion of the second ends.

It is recognized that detectable changes in impedance may include parasitic impedances from sources other than the desired impedance associated with nano-sensors 204. Parasitic impedances reduce the signal to noise ratio of detectable impedance from the nano-sensors 204 and therefore decrease the sensitivity of detection.

The horizontal implementation of the nanoneedles on the base allows impedance detection circuits to be integrated onto the same die in close proximity to the sensing tip of nano-sensors. In this manner, the length of the signal path between the sensing tip of a nano-sensor and the impedance detection circuit can be reduced to limit the introduction of external noise sources.

The nano-sensor arrays illustrated in FIG. 1 and FIGS. 2a-2d may be fabricated using the following general method. A base is provided. The base may consist solely of a substrate layer or may comprise a substrate having one or more layers of material formed on a substrate. A plurality of horizontal nano-sensors is provided along a top surface of the body. Each nano-sensor is fabricated by forming a first nanoneedle along a surface of the base, such that the first nanoneedle has a first end adjacent to or within a region. A dielectric on the first nanoneedle and a second nanoneedle is formed on the dielectric layer. The second nanoneedle is separated from the first nanoneedle by the dielectric and has a first end adjacent the first end of the first nanoneedle.

After forming the plurality of nano-sensors, a fluidic channel is etched in the base within the aforementioned region. In some embodiments, the channel is etched so that a portion of the fluidic channel will be underneath of the portion the nano-sensor that will eventually overhang the channel. After formation of the channel in the base, a cover is provided and aligned over the channel. In some embodiments, the cover may include an inverted channel formed on the bottom of the cover and aligned with the channel formed in the base. After alignment, the cover is bonded on top of the nanoneedle devices to provide a covered channel.

To assist in the detection of particles of a select target type, a selected probe molecule may be affixed at a sensing tip of the nanoneedles. The selected probe is configured to bind to particles of the target type that contact the probe. The structures used to form different probes may have different shapes and may be biological or non-biological depending on the type of molecule that is desired to be detected and may be affixed to the sensor using various known binding methods. Depending on the application, probe molecules may be affixed during manufacture of the nano-sensor, in a downstream manufacturing process, or by an end-user of a device containing the nano-sensor.

In some embodiments the nanoneedles may have an exposed surface which is composed of gold; the probe may have a thiol moiety bound to said probe. The probe may be introduced into the fluidic channel, whereby the probe may thence bind to the exposed gold surface of the nanoneedle, forming a partially covalent gold thiol bond in a thiolate-metal complex, which may be preferentially bound to the exposed portions of nanoneedles in said fluidic channel, and not in other locations in said fluidic channel. In other embodiments, the dielectric may be fabricated of a material which may be silanized. In such an embodiment, the nanoneedle and surrounding areas may be covered with a resist which is also useful to block an organofunctional alkoxysilale, prior to etching the tip of the nanoneedle. Said resist may then be utilized to prevent silanization of other portions of the nanoneedle and/or fluidic channel. The probe may be bound to a silane coupling agent such as a cyanosilane or a thiol-terminal silane. The nanoneedles ends may be etched; said probe may subsequently be introduced to the nanoneedle via the fluidic channel wherein the alkoxysilane may interact and bind to the exposed dielectric.

FIG. 3 shows a cross section of one implementation of a horizontal nanoneedle-sensor that may be used to implement a nano-sensor array. The illustrated nano-sensor is similar to nano-sensor 204 illustrated in FIG. 2d. The nano sensor is formed along a top surface of base 302 with a portion of the nano-sensor overhanging a channel 324 formed in a region of the substrate. The nano sensor includes first 310 and second 308 conductive nano-needles separated by a dielectric 306. In this example implementation, a second dielectric 304 is formed below the first nanoneedle 310 and a passivation layer 312 is formed over the second nanoneedle stack. Alternately, the dielectric coating can be formed over the nanoneedle surfaces in the channel and then the sensor location can be uncovered by local removal of the dielectric.

FIGS. 4a-4d illustrate electrical models of the nano-sensor illustrated in FIG. 3. FIG. 4a shows a circuit diagram of an electrical model of the horizontal nanoneedle-sensor shown in FIG. 3. The resistance of conductive nanoneedle layers is represented by $R_{p1}$ and $R_{p2}$. $C_{ox}$ and $C_{frg}$ correspond to the capacitance of dielectric layers and fringing capacitance respectively. The exposed end portion of the nanoneedle experiences two double layer capacitances ($C_{dl1}$ and $C_{dl2}$) between electrode interfaces, formed at endpoints C and D, when an ionic solution is present. Double layer capacitance depends on the ionic concentration and metallic (conductive) surface area [e.g. 0.20 uF/mm2 for PBS 50 mM]. Ionic resistance of the solution is shown with Rpbs, which varies with the type and concentration of ionic solution, bio-molecule concentration, the geometry of the fluidic channel, and the thickness of middle oxide layer. The sensitivity of the nanoneedle may be tuned to better detect the double layer capacitance ($C_{dl1}$ and $C_{dl2}$), or the resistance associated with the sensing region ($R_{pbs}$), by selecting the frequency of operation, permitting detection of different moieties with different binding conditions and conductivities.

Operation of the nano-sensor may include two or more phases which could include: a loading phase and a detection phase. In the loading phase, the probe is immobilized by the nano-sensor. The capturing and binding of target bio-molecule with the probe molecule is called detection phase. The following examples are describe with reference to these two phases for ease of description. It is understood that operation of the nano-sensor may include additional phases as well, including: wash steps to remove bound target, incubation time interval to permit time for binding, etc.

FIG. 4b shows a circuit diagram of an electrical model of the impedance between endpoints A and B of the horizontal nanoneedle-sensor shown in FIG. 3. This model illustrates the modulation of impedance that results from a target molecule binding with the sensor. Depending on the number, conductivity and size of target molecules bound to the sensor, and the bulk resistivity of the reagent solution, the nano-sensor will exhibit a resistance and capacitance between endpoints A and B related to the number of particles bound to the nano-sensor. FIGS. 4c and 4d illustrate two binding scenarios that may occur depending on the size of molecules and ionic concentration of the sample. FIG. 4c shows a circuit diagram illustrating the electrical behavior of the horizontal nanoneedle-sensor shown in FIG. 3 resulting from a first particle binding scenario. In this scenario, a target molecule may bind to the surface of nanoneedle at the double-layer area 320. As a result of the binding of the target molecule(s), ions are relocated and shield the surface of electrode ($C_{dl1}$, $C_{dl2}$). In some embodiments, target molecules may not bind directly to the surface of the nanoneedle, or to probes attached thereto, but may instead bind or react within the sensing region of the nanoneedle, for example, on a bead or particle 322 which is positioned, held or bound such that the bead or a portion thereof is held within the sensing region of the nanoneedle.

FIG. 4d shows a circuit diagram illustrating the electrical behavior of the horizontal nanoneedle-sensor shown in FIG. 3 resulting from a second particle binding scenario. In this second scenario, which may be more common in some biosensing applications, the target molecules may bind to the sensor outside of a shielded layer from the needle's surface at locations such as 322. In this scenario, the impedance is changed as a result of a target molecule being in close proximity to the nano-sensor.

It is recognized that a target molecule may bind to either the surface of the nano-sensor (loading phase) or to the probe molecule affixed to the sensor (detection phase). In both cases, in addition to the change of double-layer capacitance, ionic conductivity of the solution may change due to change of local ionic concentration of the solution around the needle's surface. As a result of depletion or accumulation of cations or anions, the Rpbs is changed. The resistive modulation is typically dominant in comparison to the double layer capacitance. This is true if the entire solution (the bulk) has its conductivity changed. If conductivity is locally changed, the conductivity will change only briefly.

The above electrical models and description thereof are provided for illustrative purposes and are not intended to represent fully accurate models of the impedance modulation or prescribe to any particular theory of operation.

The parasitic capacitance of the shank of the needle and the connection to the sense amplifier may limit the sensitivity of the nano-sensor. It is recognized that decreasing the capacitance $C_{ox}$ in the model shown in FIG. 4a should cause the poles to separate from each other and create a wider frequency range for impedance detection. In one or more embodiments, the thickness of the dielectric 306 between the nanoneedles 308 and 310 is increased while maintaining a thin dielectric layer 306 at the sensor tip between endpoints C and D. In one or more embodiments the dielectric 306 separating the nanoneedles has a graduated thickness, being thinner at a first end than at a second end.

The detection limit or the minimum detectable concentration of bio-species in an injected media is a figure of merit in biosensors, which depends in part on the sensitivity (the minimum number of similar binding events to occur to get a detectable signal), the flow rate, diffusion time of target molecules, sensor geometry, binding kinetics, concentrating field effects, input concentration, inhibitory factors, depletion of input concentration levels, volume of reaction chamber, etc. Reagents may also be added to the solution to increase the conductivity of the sample. The horizontal nano-sensor exhibits a high sensitivity because impedance is modulated at a detectable level in response to a small number of binding events in the nanogap sensing area between the nanoneedles of the nano-sensor. Because fewer target molecules are required for the detection, the presence of target molecules may be detected at very low concentrations on the order of 500 aM.

Figure 5A:
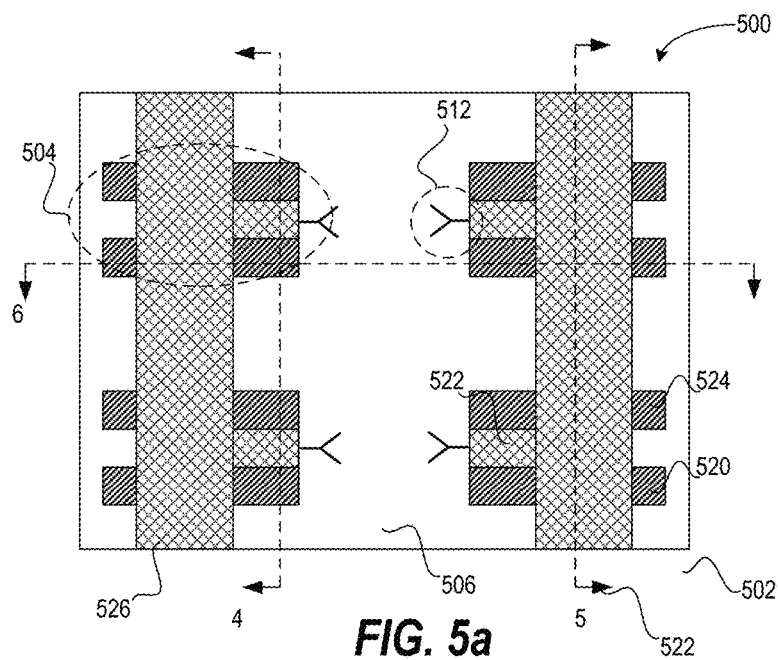
FIG. 5a shows a top view of a third nano-sensor array having a plurality of horizontal nano-sensors.
Figure 5B:
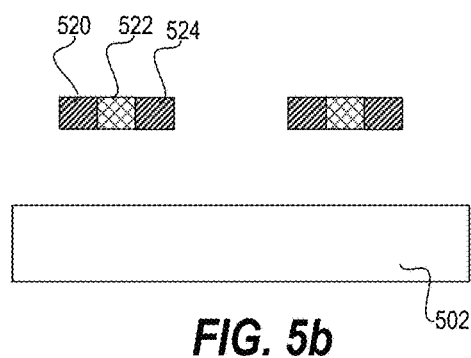
Figure 5C:
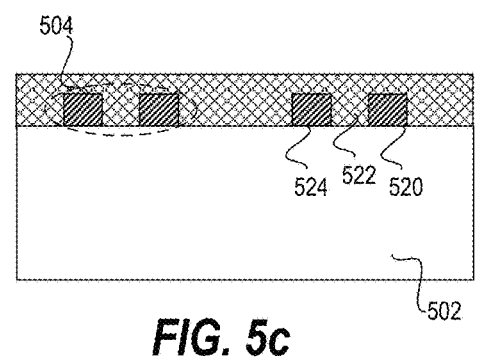
Figure 5D:
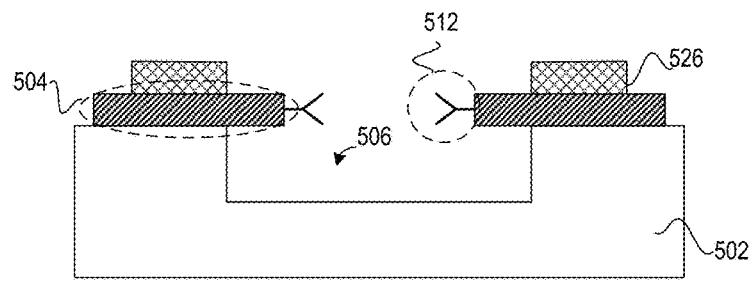

The examples herein are primarily illustrated and described with reference to nano-sensors including a nanoneedle/dielectric/nanoneedle arrangement formed in a vertical stack on a substrate base. It is understood that the horizontal nanoneedles may also be implemented in a number of other configurations as well. For example, FIGS. 5a-5d show an alternate embodiment of the structure shown in FIG. 1, where both nanoneedles of each sensor are formed along the surface of the base. FIG. 5a shows a top view of another nano-sensor array having a plurality of horizontal nano-sensors; FIG. 5b shows cross section 4 of the nano-sensor array shown in FIG. 5a; FIG. 5c shows cross section 5 of the nano-sensor array shown in FIG. 5a; and FIG. 5d shows cross section 6 of the nano-sensor array shown in FIG. 5a. Similar to the nano-sensor array 200 shown in FIGS. 2a-2d, nano-sensor array 500 includes base 502 with a channel 506 formed in the substrate. The base may consist solely of a substrate layer or may comprise a substrate having one or more layers of material formed on the substrate.

A plurality of nano-sensors 504 is formed horizontally on the base 502, wherein each nano-sensor may overhang a portion of the channel 506. Each nano-sensor 504 is also configured to include a probe 512 on a portion of the nano-sensors 504 that overhangs the channel 506 (probe 512 not shown in cross sections). During operation, a sample to be tested passes into the channel and particles that are the target type (not shown) bind with the probes upon contact.

The horizontal nano-sensors 504 are implemented with a first nanoneedle 520, a dielectric 522, and second nanoneedle 524 arranged adjacent to one another in the same layer above the base 502, with the dielectric 522 separating the first 520 and second 524 nanoneedles. In this example implementation, both nanoneedles of each nano-sensor 504 are formed along a surface of the base 502. In this illustrated implementation, the dielectric 526 is formed in between and over the nano-sensors 504, and provides a vertical extension to the sidewalls of the channel 506. Like the nanoneedles sensors 204 illustrated in FIGS. 2a-2d, a second end of each of the nanoneedles 520 and 524 is left exposed and may be used as terminals to measure impedance between the nanoneedles and may also form a base for contact pads (not shown). In some embodiments, an optional passivation or oxidation layer(s) (not shown) may be formed to cover various portions of the nanoneedles to reduce the surface area of the nanoneedle which may be available for binding or interaction with the fluid.

Current biosensors are implemented in a manner that restricts diffusion and/or detection of target molecules to a two-dimensional plane, such as on an optical slide. It is recognized that the channel may be implemented to any of a variety of different depths. In one or more embodiments, the channel may be implemented with a depth that allows particles to diffuse in a 3-dimensional space. Due to the suspended geometry of the needle in the channel, diffusion takes place in three dimensions, which results in a higher rate of binding of target molecules to the probe molecule/sensor, and thus a faster detection platform.

Figure 6:
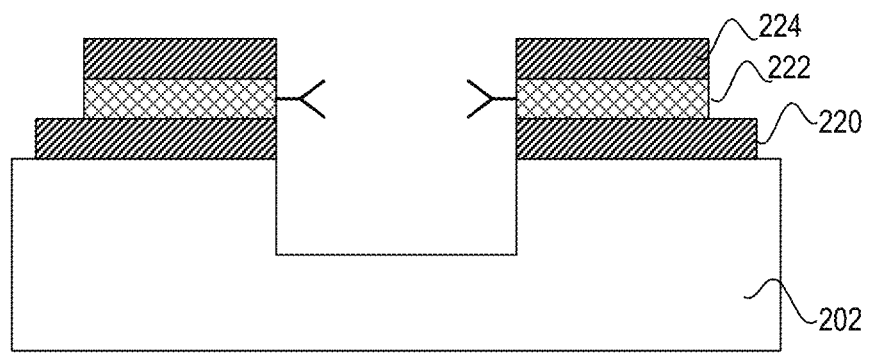
FIG. 6 illustrates a cross-section view of an alternative embodiment of the nanoneedle structure shown in FIG. 2d, wherein ends of nano-sensors are flush with the wall of a channel formed in the base.

The examples herein are primarily illustrated and described with reference to nano-sensors overhanging the channel formed in the base. It is envisioned that the sensors may be implemented overhanging the channel, flush with the walls of the channel, or any combination thereof. FIG. 6 illustrates a cross-section view of an alternative embodiment of the nanoneedle structure shown in FIG. 2d, in which ends of nano-sensors 204 are flush with the wall of a channel formed in the base. In yet some other embodiments, the plurality of nano-sensors may be implemented such that different ones of the nano-sensors overhang the channel by different lengths, or that some overhang, and others do not. The variation of the overhang length increases the distribution of the sensors in the channel, which is likely to increase target binding rate. Similarly, different sensors may be implemented to be located at different heights.

Figure 7:
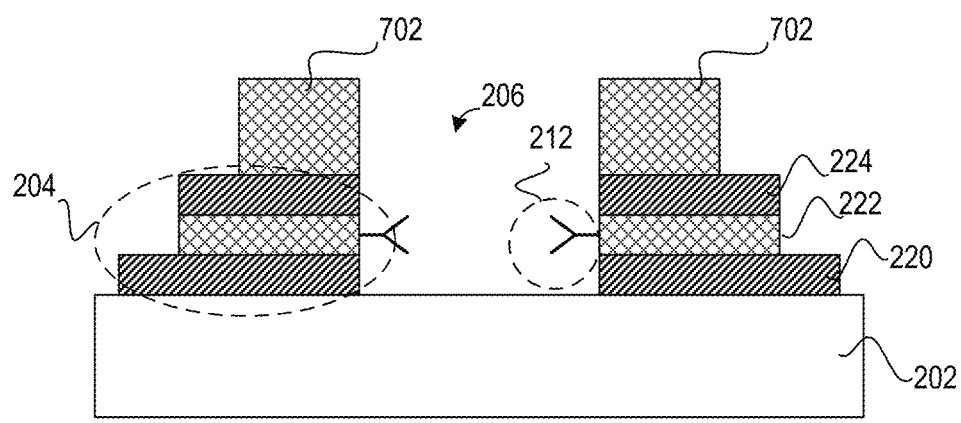
FIG. 7 illustrates a cross-section view of an alternative embodiment of the nanoneedle structure shown in FIG. 2d, wherein the channel is implemented by sidewalls formed above the base.

FIG. 7 illustrates a cross-section view of an alternative embodiment of the nanoneedle structure shown in FIG. 2d, wherein the channel is implemented by sidewalls formed above the substrate. In this illustration, the channel 206 is not formed in the base 202. The channel 206 is formed by depositing material 702 on the substrate and over the nano-sensors 204 to form sidewalls of the channel 206.

Figure 8:
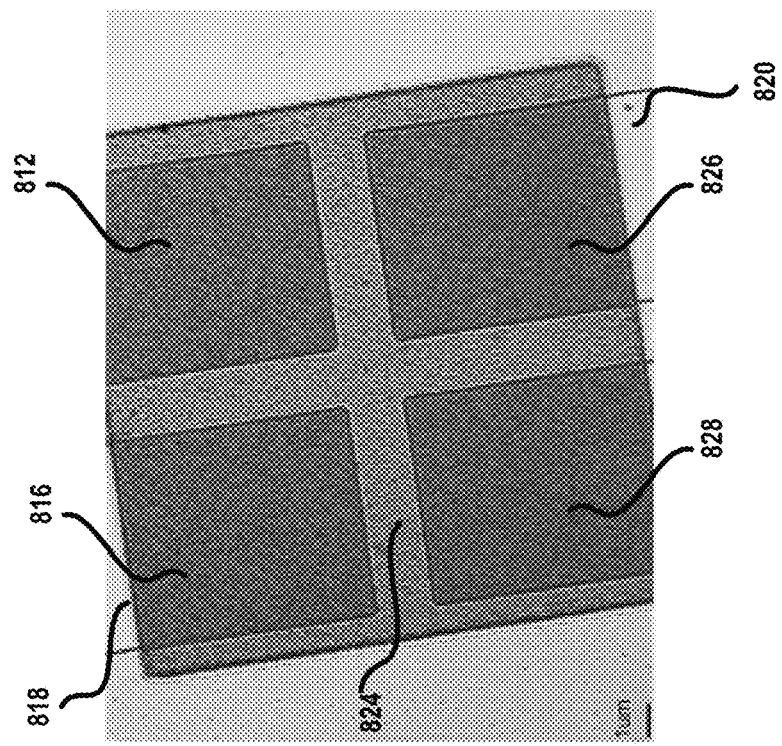
FIG. 8 illustrates the structure and the micrograph of a single and of double nanoneedles.
Figure 8:
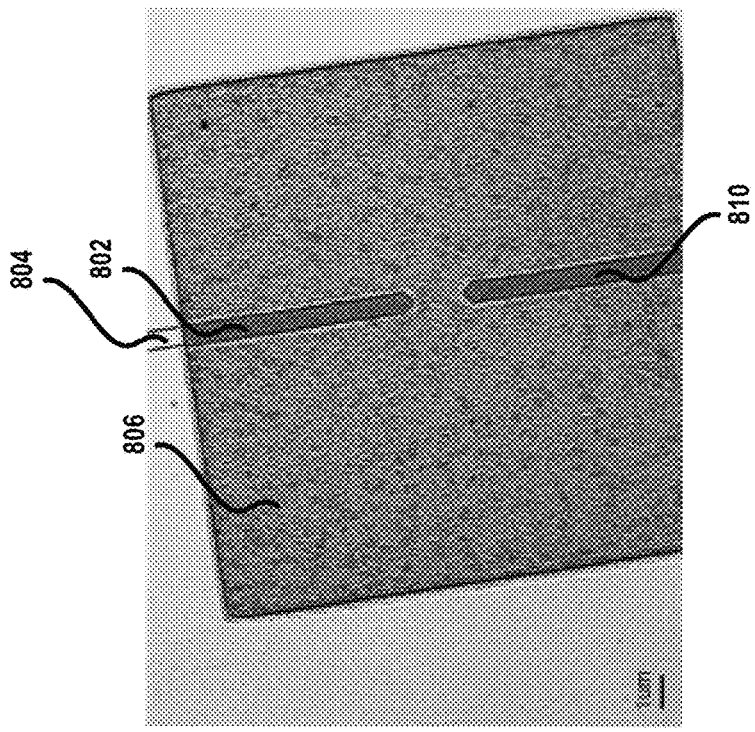

FIG. 8 illustrates a top view of double and quad nanoneedles. On the left, two of the nano-sensors 802 and 810 are formed on a body 806 as discussed above. On the right, four nano-sensors 812, 816, 826, and 828 are formed on a substrate.

In order to minimize parasitic capacitance, nanoneedles may be fabricated such that they have thin regions of dielectric close to the sensing regions, and thicker regions farther from the sensing region. These differences in the thickness of different portions of the nanoneedles may be formed by applying a first nanoneedle, followed by a uniform layer of dielectric applied over said first nanoneedle. An etch resist may then be applied over portions of the nanoneedle, and may also be applied over portions of the adjacent silicon. Thinner portions of nanoneedles 802 and 810 are thinner portions of the dual nanoneedles, while thinner portions of nanoneedles 812, 816, 826 and 828 are thinner portions of quad nanoneedles, formed by etching, including etching regions of silicon adjacent to dual nanoneedle 806, and regions adjacent to quad nanoneedle 824; Those portions of the nanoneedles which are not etched and which are illustrated include thicker portion of dual nanoneedle 818 and thicker portions of nanoneedles 818, 820.

The nanoneedles of the nano-sensors may be formed using any one of a number of lithography techniques. One method suitable for formation of the horizontal nanoneedles is known as electron-beam lithography (EBL). In EBL, a resist layer is formed on a silicon substrate. The resist layer is exposed with a beam of electrons in a patterned fashion across the surface of the resist layer. Following patterning, the resist layer is developed by selectively removing either exposed or non-exposed regions of the resist layer to form patterned channels in the resist layer, which may form a mask for the nanoneedles.

Depending on the materials used, the nanoneedles may be formed using a number of methods recognized by those skilled in the art e.g. electroplating, chemical vapor deposition (CVD), etc. In another example implementation, an etch step may be performed to etch a conductive layer below the patterned resist layer to form the nanoneedles. Other possible patterning and etching methods are envisioned as well.

EBL is not limited to the diffraction limit of light and allows photo-patterning techniques to create features in the nanometer range. It is understood that the EBL process may be implemented using a number of different configurations utilizing different electron beam energies, various resist materials, and various chemical etch techniques.

In one example EBL implementation, a silicon substrate is cleaned, coated with 100 nm thick 2% 950K Poly Methyl Methacrylate positive tone electron beam resist, and soft baked for 120 s at 200° C. An electron beam having at an acceleration voltage of 10 kV and an electron dose of 100 $\mu C/cm2$ may be used to pattern the resist layer. After EBL exposure, the resist is developed by soaking in a methyl isobutyl ketone/isopropyl alcohol (MIBK/IPA) 1:3 by volume solution for 30 s at 18° C., and then rinsed with pure 2-propanol for 30 seconds. It is recognized that the width of the patterned channels, and the resulting nanoneedles, varies with different dose factors (e.g. Single Pixel Lines (SPL) measuring 20 nm at SPL dose=345 pC/cm). The minimum width of continuous etched SPL was measured as 8.93 nm (FIG. 7, d) but it results in high LER (line edge roughness).

The nanoneedles may be formed using a number of different conductive materials including, e.g., p+-silicon, Al, Au, etc. For ease of description, the examples herein are primarily described with reference to nanoneedles formed using p+ silicon as the conductive material.

The following example describes one possible implementation for manufacturing nanoneedles with p+ silicon. 250 nm of silicon oxide is thermally grown on the silicon substrate, followed by the deposition of 100 nm of polysilicon, then doped with phosphorus to achieve a sheet resistance of 210 ohms per square. (It was reduced to 30 ohms per square using alternative doping approaches.) This p+-silicon layer is coated with 30 nm of SiO2 followed by another p+-silicon layer deposition. Finally, a 20 nm SiO2 layer covers the top p+-silicon layer. A three step lithography process is performed, followed by etching that includes: a 1.6 um SHIPLEY 3612 resist spin-coated (SVG coat), and after lithography (using a Karl Suss mask aligner) and baking for 120 sec, the resist is baked and developed (SGV Photoresist Developer). Then the combination of the 20 nm top-SiO2 layer, the 100 nm top p+-silicon layer, and the 30 nm middle oxide layer down to the bottom p+-silicon layer, are dry-etched (Applied Materials Precision 5000 Etch). In the second lithography step, the remaining 100 nm bottom p+-silicon layer and 200 nm bottom SiO2 layer as well as 1 um deep in the substrate silicon is dry-etched followed by a XeF2 injection to etch and open the channel underneath of the nanoneedle devices. Finally, the 20 nm top silicon layer is removed from the pad areas to enable contact access for measurement and testing.

The manufacturing implementation using p+ silicon to form nano-wires described above is provided for illustrative purposes only. The thicknesses, selection of materials, and other process specifics are intended only for illustration and not limitation.

The embodiments are thought to be applicable to a variety of applications, which utilize particle detection. For example, on-chip amplification of electrical signals and impedance detection circuits may be integrated alongside the nano-sensor arrays to provide lab-on-a-chip diagnostics for portable devices and are thought to have useful clinical applications for detection of several biomarkers in early stage diagnoses, and in the field diagnostics. Other aspects and embodiments will be apparent to those skilled in the art from consideration of the specification. It is intended that the specification and illustrated embodiments be considered as examples only, with a true scope and spirit of the invention being indicated by the following claims.

What is claimed is:

1. A method for sensing, the method comprising:
by using a channel proximate to a base, guiding particles through the channel via fluidic pressure;
providing a plurality of nano-sensors, wherein each of the plurality of nano-sensors includes a first nanoneedle and a second nanoneedle, the first and second nanoneedles being separated by a solid state dielectric and having ends that are adjacent to one another, and the second nanoneedle is disposed vertically above the first nanoneedle in relation to the base; and
using a detection circuit, coupled to each of said nanoneedles, to detect a change in impedance between the first and second nanoneedles of each nano-sensor that results from a binding of a target particle to a respective probe.

2. The method of claim 1, wherein for each of the plurality of nano-sensors, a probe is used proximate to an exposed portion of the solid state dielectric between the first and second nanoneedles at a first end of the second nanoneedle, the probe being used to bind to said target particle.

3. The method of claim 2, wherein the probe is provided on one of the first and second nanoneedles.

4. The method of claim 2, wherein the channel is an inverted fluidic channel that includes a cover.

5. The method of claim 2, wherein the solid state dielectric is thicker at one portion of the first and second nanoneedles than at a first end of said nanoneedles.

6. The method of claim 2, wherein the second nanoneedle is disposed parallel in relation to the first nanoneedle.

7. The method of claim 2, wherein the target particle is a polynucleotide.

8. The method of claim 2, wherein for each of the plurality of nano-sensors, a probe is used proximate to an exposed portion of the solid state dielectric between the first and second nanoneedles and at a first end of the second nanoneedle, the probe being used to bind to said target particles.

9. The method of claim 2, wherein for each of the plurality of nano-sensors, a probe is used proximate to an exposed portion of the solid state dielectric between the first and second nanoneedles and at a first end of the second nanoneedle, the probe being used to bind to said target particle, and further including using a passivation layer to reduce nanoneedle surface area available for binding or interaction with the fluid, the passivation layer being over at least the first and second nanoneedles wherein the passivation layer leaves a portion of a first end of the first nanoneedle or a first end of the second nanoneedle available for binding.

10. A nano-sensor array, comprising:
a sensing device comprising a base;
a channel proximate to the base wherein particles are passed through said channel via fluidic pressure;
a plurality of nano-sensors, wherein each nano-sensor comprises:
a first nanoneedle and a second nanoneedle, wherein the first and second nanoneedles are separated by a solid state dielectric and have ends that are adjacent to one another, and are disposed vertically in relation to one another and to the base; and
a detection circuit coupled to each of said nanoneedles, wherein the detection circuit detects a change in impedance between the first and second nanoneedles of each nano-sensor that results from a binding of a target particle to a respective probe.

11. The nano-sensor array of claim 10, wherein said probe is provided on one of the first and second nanoneedles.

12. The nano-sensor array of claim 10, further comprising a second particle bound to at least one said particle of a target type.

13. The nano-sensor array of claim 11, wherein the detection circuit determines the number of target particles bound to the respective probe.

14. The nano-sensor array of claim 11, wherein each probe in a first subset of the plurality of nano-sensors binds to a first type of target particle and each probe in a second subset of the plurality of nano-sensors binds to a second type of target particle.

15. The nano-sensor array of claim 11, wherein the second nanoneedle of each nano-sensor is disposed along a surface of the base.

16. The nano-sensor array of claim 11, wherein the second nanoneedle of each nano-sensor is disposed vertically in relation to the first nanoneedle.

17. The nano-sensor array of claim 11, wherein the first and second nanoneedles are disposed vertically in relation to the base.

18. The nano-sensor array of claim 11, wherein the solid state dielectric has a thickness of 500 nm or less.

* * * * *